US006442997B1

(12) United States Patent
Megerle et al.

(10) Patent No.: US 6,442,997 B1
(45) Date of Patent: Sep. 3, 2002

(54) RAM-AIR SAMPLE COLLECTION DEVICE FOR A CHEMICAL WARFARE AGENT SENSOR

(75) Inventors: Clifford A. Megerle, Manassas, VA (US); Douglas R. Adkins, Albuquerque; Gregory C. Frye-Mason, Cedar Crest, both of NM (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 09/969,196

(22) Filed: Oct. 1, 2001

(51) Int. Cl.[7] .................. G01N 29/02; G01N 27/26; H01L 41/04
(52) U.S. Cl. .................. 73/24.01; 204/406; 310/313 R
(58) Field of Search .............. 73/24.01, 23.2, 73/19.03, 23.34, 24.06, 31.05, 579, 609; 205/787; 204/406; 310/313 R; 422/82.02

(56) References Cited

U.S. PATENT DOCUMENTS

| 3,914,053 A | 10/1975 | Morley et al. |
| 4,182,119 A | 1/1980 | Hurley |
| 5,469,369 A | 11/1995 | Rose-Pehrsson et al. |
| 5,481,110 A | 1/1996 | Krishnaswamy et al. ... 250/288 |
| 5,517,866 A | 5/1996 | Manning et al. |
| 5,826,214 A | 10/1998 | Lieb et al. |
| 5,930,326 A | 7/1999 | Rothschild et al. |
| 6,101,886 A | 8/2000 | Brenizer et al. |

*Primary Examiner*—Hezron Williams
*Assistant Examiner*—Jay L. Politzer
(74) *Attorney, Agent, or Firm*—Simpson and Simpson (57) ABSTRACT

In a surface acoustic wave sensor mounted within a body, the sensor having a surface acoustic wave array detector and a micro-fabricated sample preconcentrator exposed on a surface of the body, an apparatus for collecting air for the sensor, comprising a housing operatively arranged to mount atop the body, the housing including a multi-stage channel having an inlet and an outlet, the channel having a first stage having a first height and width proximate the inlet, a second stage having a second lower height and width proximate the micro-fabricated sample preconcentrator, a third stage having a still lower third height and width proximate the surface acoustic wave array detector, and a fourth stage having a fourth height and width proximate the outlet, where the fourth height and width are substantially the same as the first height and width.

8 Claims, 8 Drawing Sheets

Fig. 8

RAM-AIR SAMPLE COLLECTION DEVICE FOR A CHEMICAL WARFARE AGENT SENSOR

STATEMENT REGARDING FEDERALLY SPONSORED RESEARCH AND DEVELOPMENT

This invention was made with government support under Contract No. DE-AC04-94AL85000, awarded by the U.S. Department of Energy. The government has certain rights in the invention.

FIELD OF THE INVENTION

The present invention relates generally to chemical warfare agent sensors and, more particularly, to a ram-air sample collection device for a chemical warfare agent sensor.

BACKGROUND OF THE INVENTION

Chemical warfare agent point sensors, such as surface acoustic wave sensors and ion mobility spectrometers, are simply too heavy and large for use on many of the small unmanned aerial vehicles (UAV's). This is because these sensors all presently require a pump, such as a cyclone or rotary fan/blower to sample the air for agents. The blower/fan is by far the heaviest and largest part of the sensing apparatus.

Thus, current chemical sensors use active pumping to force gas to flow over the sensor element. Pumping is the major source of energy consumption in the devices. Using a ram-air approach, it is possible to force a sample stream to flow over a preconcentrator and sensor device using only the static pressure developed by the relative motion of an air stream to the sensor body. This system can be used in small unmanned aerial vehicles where low power consumption is required, or in other applications where air flows over a vehicle or through a duct.

What is needed, then, is a ram-air collector device that can be mounted to a chemical warfare agent sensor, and make use of the forward momentum of the UAV to force air to be sampled and tested through the sensor module.

SUMMARY OF THE INVENTION

The present invention broadly comprises a ram-air collector for a chemical warfare agent sensor, comprising a housing operatively arranged to mount atop the sensor, the housing including a multi-stage channel having an inlet and an outlet, the channel having a first stage having a first height and width proximate the inlet, a second stage having a second lower height and width proximate the microfabricated sample preconcentrator, a third stage having a still lower third height and width proximate the surface acoustic wave array detector, and a fourth stage having a fourth height and width proximate the outlet, where the fourth height and width are substantially the same as the first height and width.

The general object of the present invention is to provide a lightweight, efficient ram-air collector, operatively arranged to be mounted to a moving object or vehicle, for a chemical warfare agent or explosives sensor that eliminates the need for a blower or fan to actively pump air over the sensor.

This and other objects, features and advantages of the present invention will become readily apparent to those having ordinary skill in the art upon a reading of the following detailed description of the invention in view of the drawings and claims.

DETAILED DESCRIPTION OF THE PREFERRED EMBODIMENT

In the following detailed description of the preferred embodiment, and in the appended claims, the following terms are defined: UAV: Unmanned Aerial Vehicle. As the name suggests, these are vehicles that fly unmanned. Examples include, but are not limited to: Predator, DarkStar, Global Hawk. They are usually used to perform intelligence, surveillance and reconnaissance missions. It should be appreciated, however, that although the UAV is one possible application for the subject invention, it is not the only one, as the present invention may be mounted and used effectively on a wide variety of moving objects, including airplanes, helicopters, missiles, land vehicles, ships, and practically any other object that moves.

SAW: Surface Acoustic Wave. Acoustic wave devices have been in commercial use for over sixty years. Although the telecommunications industry is the largest user of acoustic wave devices, they are also used for chemical vapor detection. Surface acoustic wave sensors are so named because they use a mechanical, or acoustic, wave as the sensing mechanism. As the acoustic wave propagates through or on the surface of the material, any changes to the characteristics of the propagation path affect the velocity and/or amplitude of the wave. Changes in velocity can be monitored by measuring the frequency or phase characteristics of the sensor and can then be correlated to the corresponding physical quantity that is being measured. Virtually all acoustic wave devices and sensors utilize a piezoelectric crystal to generate the acoustic wave. Most SAW chemical sensors rely on the mass sensitivity of the sensor in conjunction with a chemically selective coating that absorbs the vapors of interest resulting in an increased mass loading of the SAW sensor. Bill Drafts, "Acoustic Wave Technology Sensors", Microsensor Systems, Inc., a Sawtek Company.

The present invention, in a preferred embodiment, is suitable for use with a variety of chemical warfare agent, biological warfare agent and explosive sensors. In a preferred embodiment, however, the invention is most useful in ion mobility and surface acoustic wave (SAW) sensors. SAW sensors are probably the leading microsensor technology for chemical warfare agent detection, in part because they are very flexible in tailoring the chemical selectivity of the individual sensors, and the in depth understanding of their response mechanisms. The present invention, then, in a preferred embodiment, is shown and described in combination with a SAW sensor, but it should be appreciated that the invention is useful in combination with other types of sensors, and that these applications are considered to be within the scope of the appended claims. A description of the general theory and operation of ion mobility and SAW sensors follows:

Ion Mobility Spectrometry (IMS)

Ion mobility spectrometry (IMS) was created between 1965 and 1970 from studies on ion-molecule chemistry at atmospheric or elevated pressure with mass spectrometers and from ionization detectors for airborne vapor monitoring. A conventional ion mobility spectrometer consists of two main areas: the reaction region and the drift region. In the reaction region, atmospheric pressure carrier gas (clean, dry air) is ionized by collision of beta particles from a weak nickel-63 source with nitrogen and oxygen. These reactant ions then undergo ion/molecule reactions with the explosive/chemical warfare agent molecule. The explosive/chemical warfare agent molecules also undergo other ion forming reactions such as adduct formation and dissociation reactions.

Under the influence of an electric field, the mixture of reactant and product ions reaches a shutter grid that separates the reaction region and the drift region. The shutter grid is made up of sets of thin mesh wires with a bias voltage between them. With the bias voltage applied, the ions are attracted to the gating grid and lose their charge. Then the grid bias is briefly turned off, and ions are transmitted into the drift region of the cell. The ions are then focused and accelerated by an electric field (typically 1,000 to 3,000 volts) along the drift region (typically 8 centimeters) to arrive at the collector electrode (typically in a time of 10 to 20 milliseconds). The smaller, compact ions have a higher mobility than the heavier ions, and therefore traverse the region and collide with the collector plate in a shorter time. The collector current is then amplified; its magnitude, as a function of time, is proportional to the number of ions arriving at that moment.

In an IMS explosives/chemical warfare agent detection system, times required for ions of specific explosives to drift down the IMS tube are precisely known and are programmed into the system's microprocessor. The microprocessor monitors the collector electrode signal at the programmed drift times to detect the presence of explosive/chemical warfare molecule ions. Typical analysis cycles require 5 to 8 seconds from introduction of sample to alarm notification.

Some systems combine IMS with a front-end gas chromatography (GC) in order to optimize selectivity.

Several manufacturers presently offer drug detection as a standard or optional feature on their IMS detectors. Be aware that in many cases the unit must be powered down momentarily to switch between the drug and explosives detection modes. Trends in IMS technology are to continue miniaturization of detection instruments and incorporate a nonradioactive ionization source.

Gas Chromatography/Surface Acoustic Wave (GC/SAW)

Another type of technology used for explosives and chemical warfare agent detection utilizes a portable gas chromatograph (GC) equipped with a surface acoustic wave (SAW) detector. In a SAW-based GC system, the SAW resonator crystal is exposed to the exit gas of a GC capillary column by a carefully positioned and temperature-controlled nozzle. When condensable vapors entrained in the GC carrier gas impinge upon the active area between the resonator electrodes, a frequency shift occurs in proportion to the mass of the material condensing on the crystal surface. The frequency shift is dependent upon the properties (mass and the elastic constants) of the material being deposited, the temperature of the SAW crystal, and the chemical nature of the crystal surface.

A thermoelectric cooler maintains the SAW surface at sufficiently low temperatures to ensure a good trapping efficiency for explosive vapors. This cooler can be reversed to heat the crystal in order to clean the active surface (boil off adsorbed vapors). The temperature of the SAW crystal acts as a control over sensor specificity based upon the vapor pressure of the species being trapped. This feature is useful in distinguishing between relatively volatile materials and sticky explosive materials.

During a sampling sequence, vapor samples are drawn through the GC inlet from a preconcentrator and then pumped through a cryo-trap. The cryo-trap is a metal capillary tube held at a temperature low enough to trap explosive vapors, while allowing more volatile vapors to pass through. After passing through a second cryo-trap the sample is injected into the GC column and separated in time by normal column operation for species identification. As the constituent vapors exit the column, they are collected and selectively trapped on the surface of the SAW crystal, where the frequency shift can be correlated to the material concentration.

Total analysis time, including preconcentration of the vapors, is typically 10 to 15 seconds. Sensitivity to picogram levels of explosives has been shown by the manufacturer of the only commercially available system. The system is portable, about the size of a large briefcase. Cost is similar to an ECD system, and the system is operational within 10 minutes of setup.

The present invention is not limited to any specific surface acoustic wave sensor. The Surface acoustic wave sensor may be of a type manufactured by Sawtek Incorporated of Orlando, Fla. or be of a type similar to the "chemlab-on-a-chip" microsensor ($\mu$Chemlab™) of Sandia National Laboratories. This device is a Sandia initiative to build a hand-held "chemistry laboratory" the size of a palm-top computer. The acoustic wave sensor is one piece of equipment in that laboratory (and quite a bit smaller than a palm-top computer). The sensor is so small, in fact, that an array of as many as four or five miniature sensors, each about two millimeters by 0.5 millimeters, by 0.5 millimeters and sensitive to different chemicals, can be built on a chip the size of a shirt button. Another possible sensor is described in U.S. Pat. No. 5,469,369 (Rose-Pehrsson et al.), incorporated herein by reference. Finally, the sensor could be of the type of chemical or biological warfare sensors described in U.S. pat. application Ser. No. xx,xxx,xxx, filed on August xx, 2001, and entitled, "SECURITY SYSTEM FOR NBC-SAFE BUILDING", incorporated herein by reference.

Figure 1:
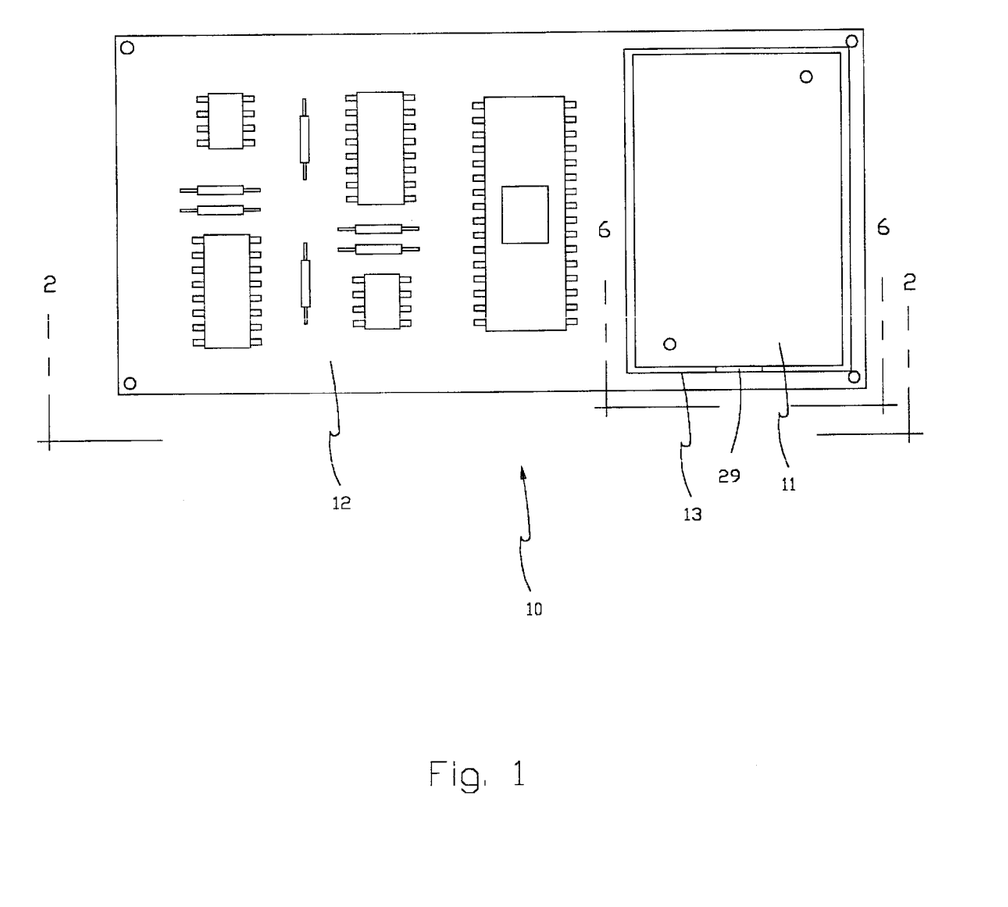
FIG. 1 is a top plan view of a typical sensor with the apparatus of the invention mounted thereto.
Figure 2:
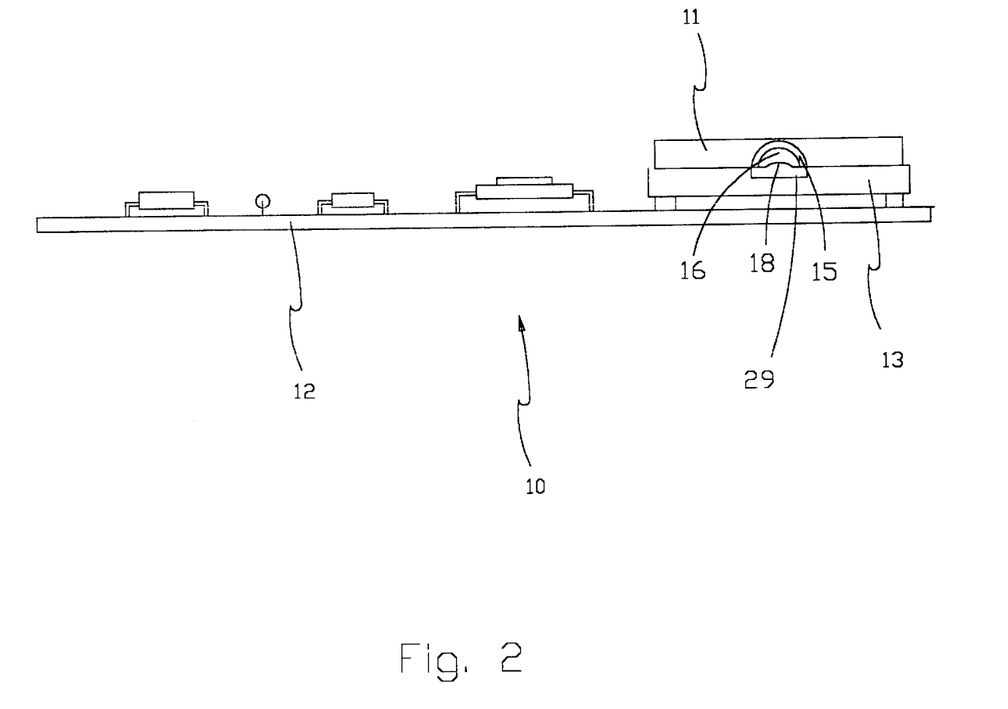
FIG. 2 is a side view of the apparatus shown in FIG. 1, taken generally along line 2—2 of FIG. 1.
Figure 3:
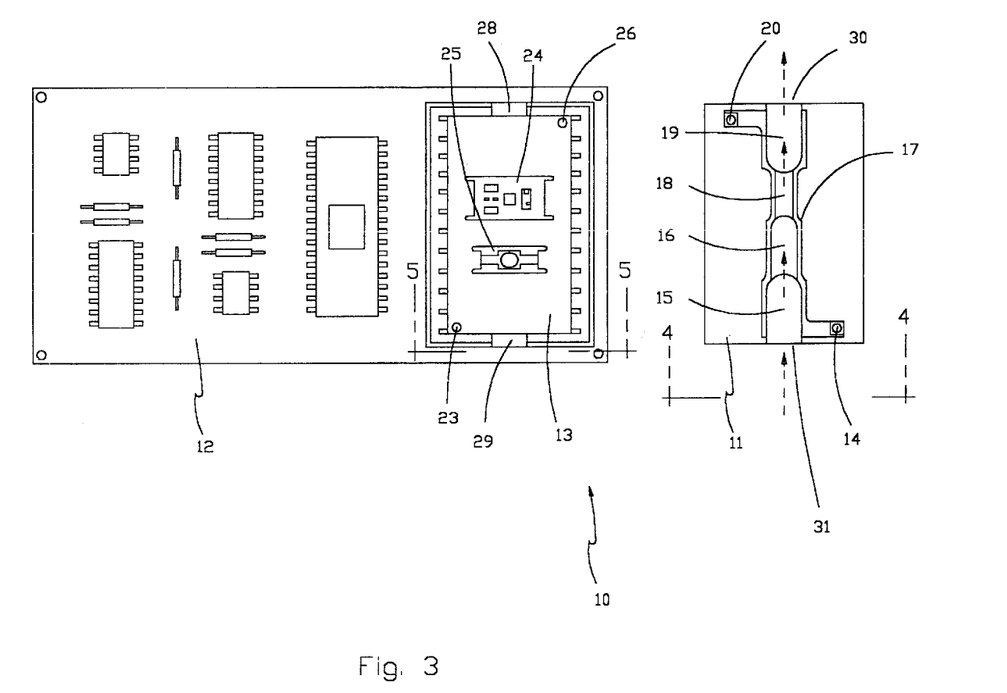
FIG. 3 is a top plan view of the top of the sensor shown in FIG. 1 (on the left) and a bottom plan view of the apparatus of the invention (on the right), removed from the sensor and flipped on its top side.

The theory of operation of surface acoustic wave sensors is described supra, and an illustration of a typical surface acoustic wave sensor 10 appears in FIGS. 1 and 3. The actual sensor is labeled 13 in the drawing —the other components in module (printed circuit board) 12 are associated electronics. As shown in FIG. 2, sensor 13 includes a body which is mounted to circuit board 12. Ram-air collector 11 is shown in both FIGS. 1 and 2 mounted atop sensor 13. In a preferred embodiment, the collector body is made of a ceramic material, compatible with hybrid microcircuit packaging methods when the body of the package is also ceramic. However, it should be apparent to those having ordinary skill in the art that it would be possible to mount everything in a plastic package, so the collector body could easily be made of plastic. Although ceramic and plastic are the two most likely materials for the collector, metal is also a possibility for both the collector and the package itself Also in a preferred embodiment, the collector may be secured to the sensor by any suitable means, such as by mounting screws, or by adhesive (epoxy), for example. In the embodiment shown, a gasket, not shown, would be placed between the ram-air collector and the sensor, and a first mounting screw (not shown) would pass through aperture 20 in the collector (shown in FIG. 3) and threadably engage partial threaded through bore 26 in the sensor body, and a second mounting screw (not shown) would similarly pass through aperture 14 of the collector and threadably engage partial threaded through bore 23 of the sensor body.

Figure 4:
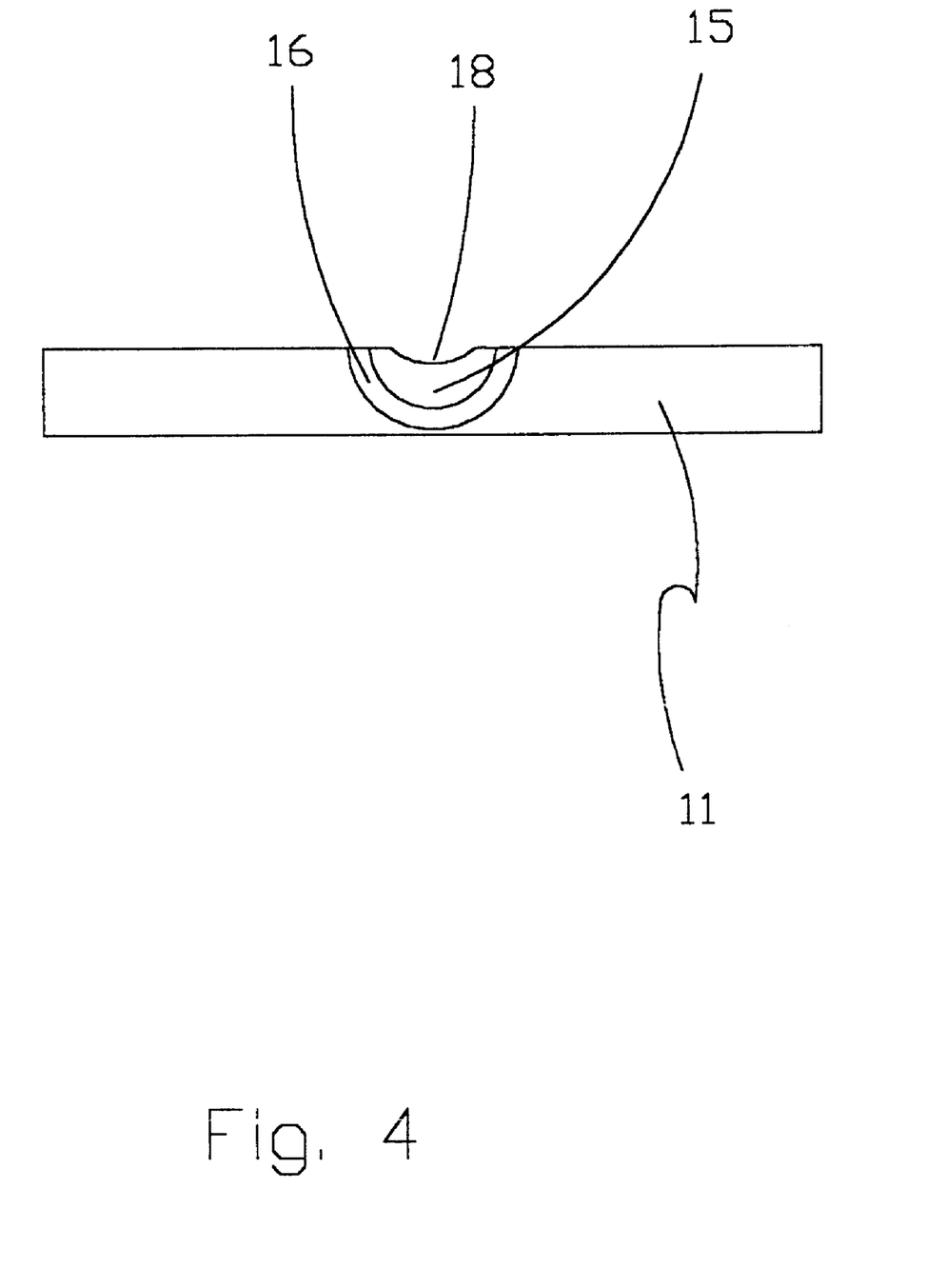
FIG. 4 is an end view of the apparatus of the invention, taken generally along line 4—4 of FIG. 3.
Figure 6:
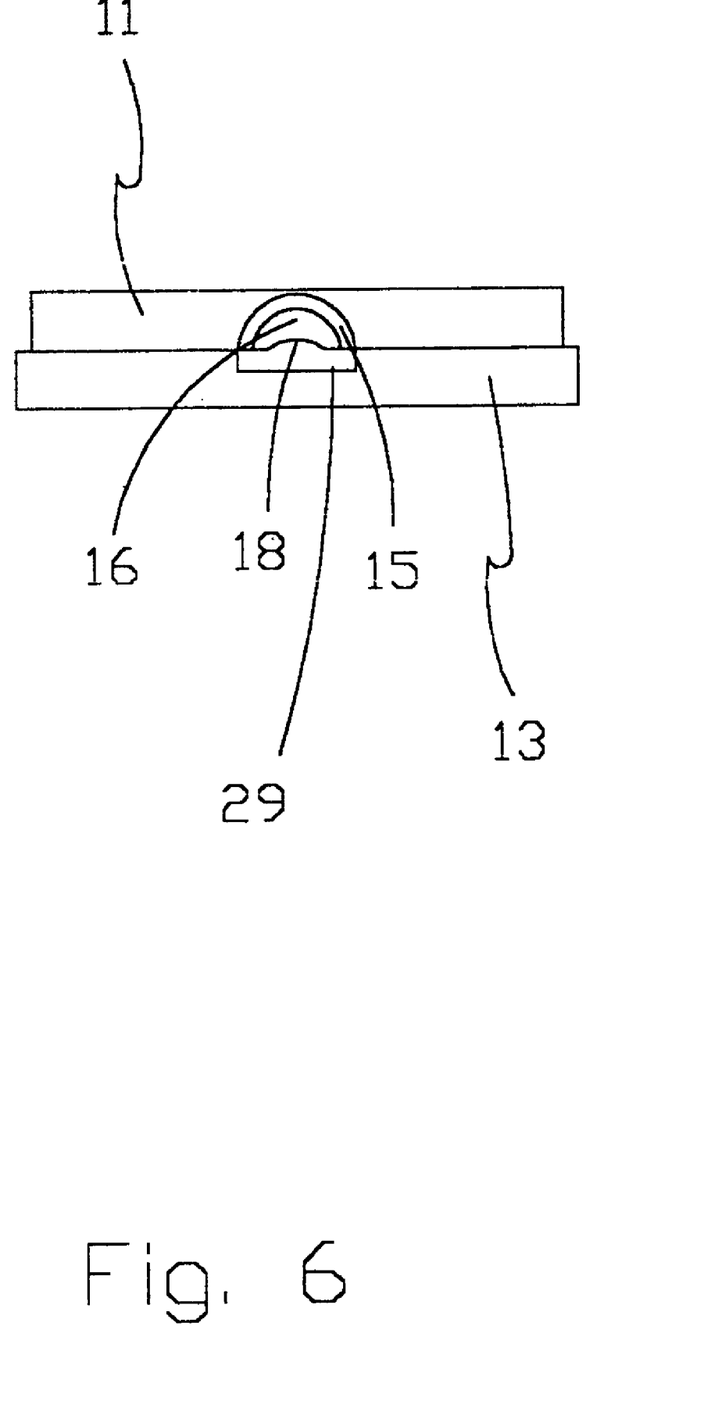
FIG. 6 is a view similar to that of FIG. 5, but with the apparatus of the present invention in place atop the sensor.

FIG. 3 is a plan view of the sensor with the ram-air collector removed and flipped on its back. In this view, sensor 13 is seen to include micro-fabricated sample preconcentrator 25 and surface acoustic wave array detector 24. Ram-air collector 11 is shown in this drawing removed from the sensor and "flipped" on its back. Collector 11 is seen to include channel or passageway 17, through which sampled air travels in the direction indicated by the dotted arrows. Channel 17 is seen to comprise first section 15, second section 16, third section 18 and fourth section 19. First section 15 is proximate inlet 31, and fourth section 19 is proximate outlet 30. As seen in the drawing, first section 15 is wider than second section 16. As seen in FIGS. 4 and 6, first section 15 also has a greater height than that of second section 16. In other words, the cross-sectional area of first section 15 is greater than the cross-sectional area of second section 16. Thus, the air sample is forced through an air-space of reduced volume in section 16 as opposed to section 15. Similarly second section 16 is wider than third section 18, and, as shown in FIGS. 4 and 6, second section 16 also has a greater height than third section 18. In other words, the cross-sectional area of second section 16 is greater than that of third section 18. Thus, the air sample is forced through an air-space of reduced volume in section 18 as opposed to section 16. In a preferred embodiment, the width, height and cross-sectional area of fourth channel section 19 is identical to that of first section 15, although the collector would also work if fourth channel section 19 had dimensions which were not identical to those of first channel section 15, as long as the cross-sectional area of section 19 is larger than that of third section 18. In a preferred embodiment, second section 16 of the channel is in register with preconcentrator 25, and third section 18 is in register with SAW detector 24. By "in register" we mean that those particular sections of the channel are aligned with the preconcentrator and detector, respectively, such that air in those particular second and third channel sections are in direct communication with the preconcentrator and detector, respectively. In operation, the detector and collector assembly would be mounted to a moving object, such as a vehicle, such that inlet 31 would face the direction of travel, thereby forcing air into the inlet of the channel.

Figure 5:
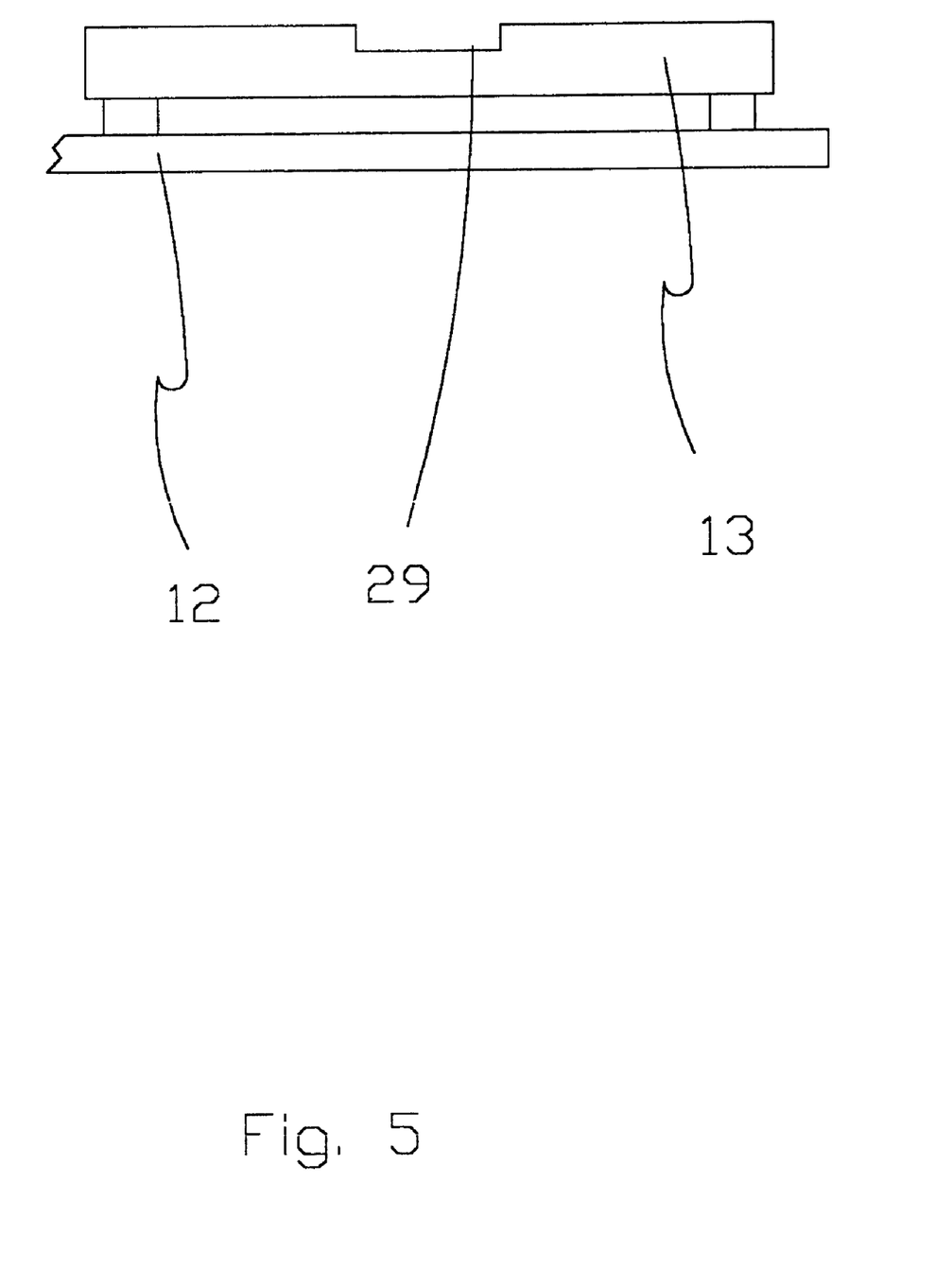
FIG. 5 is a fragmentary end view of the typical sensor shown in FIG. 1, with the apparatus of the present invention removed.

FIG. 5 is a fragmentary view of circuit board 12 illustrating how sensor 13 is mounted to the board. This view also shows rabbet 29 in the body of the sensor, which rabbet aligns with channel 17 when the collector is in place, and together form inlet 31, as best shown in FIG. 6 (FIG. 6 is an end view which shows the collector in place atop the sensor.)

Theory of Operation

The basic device 11 of the invention is a gas scoop that is illustrated in various drawing FIGS. The wide inlet first section 15 (bottom of FIG.) is directed toward an oncoming stream and the discharge fourth section 19 of the device (FIG. top) is connected to a low pressure region in the flow around sensor 13. The pressure difference between the inlet and the discharge (outlet) of the scoop drives gas over the preconcentrator and the surface acoustic wave (SAW) chemical sensor.

The maximum pressure that can be developed between the inlet and discharge is on the order of $\frac{1}{2}\sigma V^2$ where $\sigma$ is the air density and $V$ is the relative velocity between the sensor housing and the surrounding air. With a 30 knot air speed, the pressure difference is about 0.02 psi (150 Pa).

Figure 7:
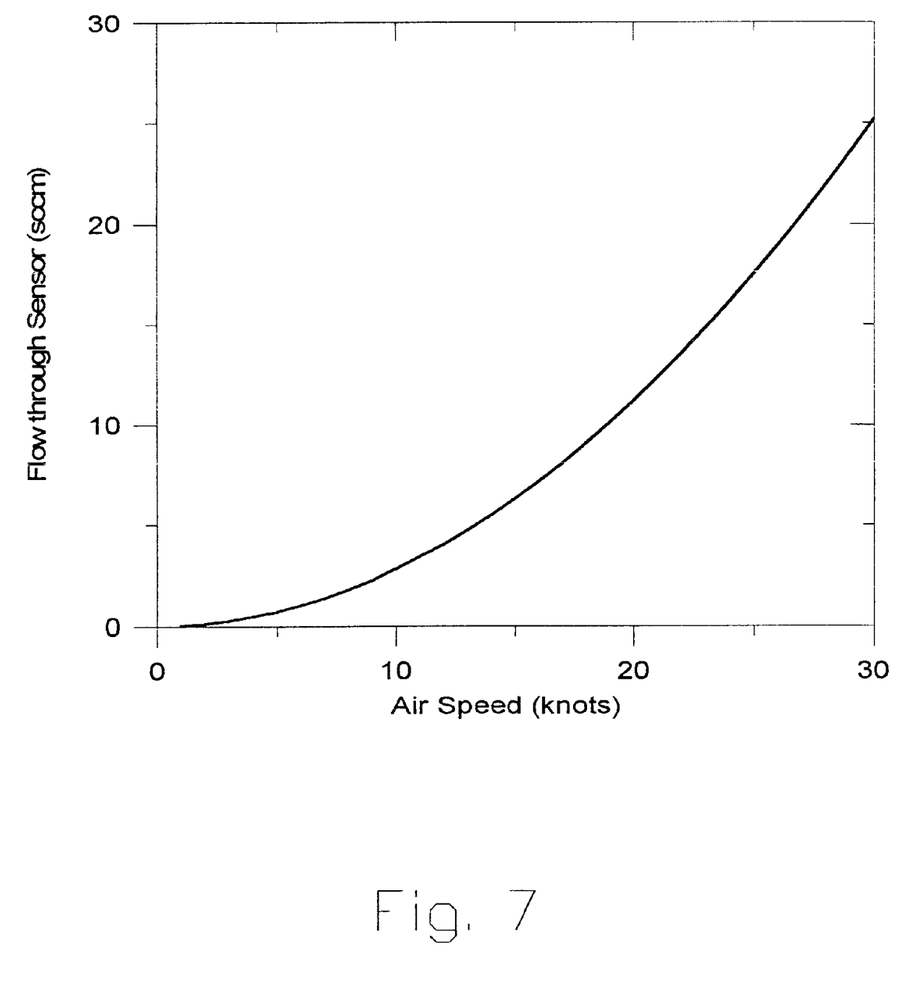
FIG. 7 is a graph illustrating estimated flow through the ram-airflow duct of the invention as a function of air speed; and, FIG. 8 is a graph illustrating the measured SAW signal for three preconcentrator collection times.
Figure 8:
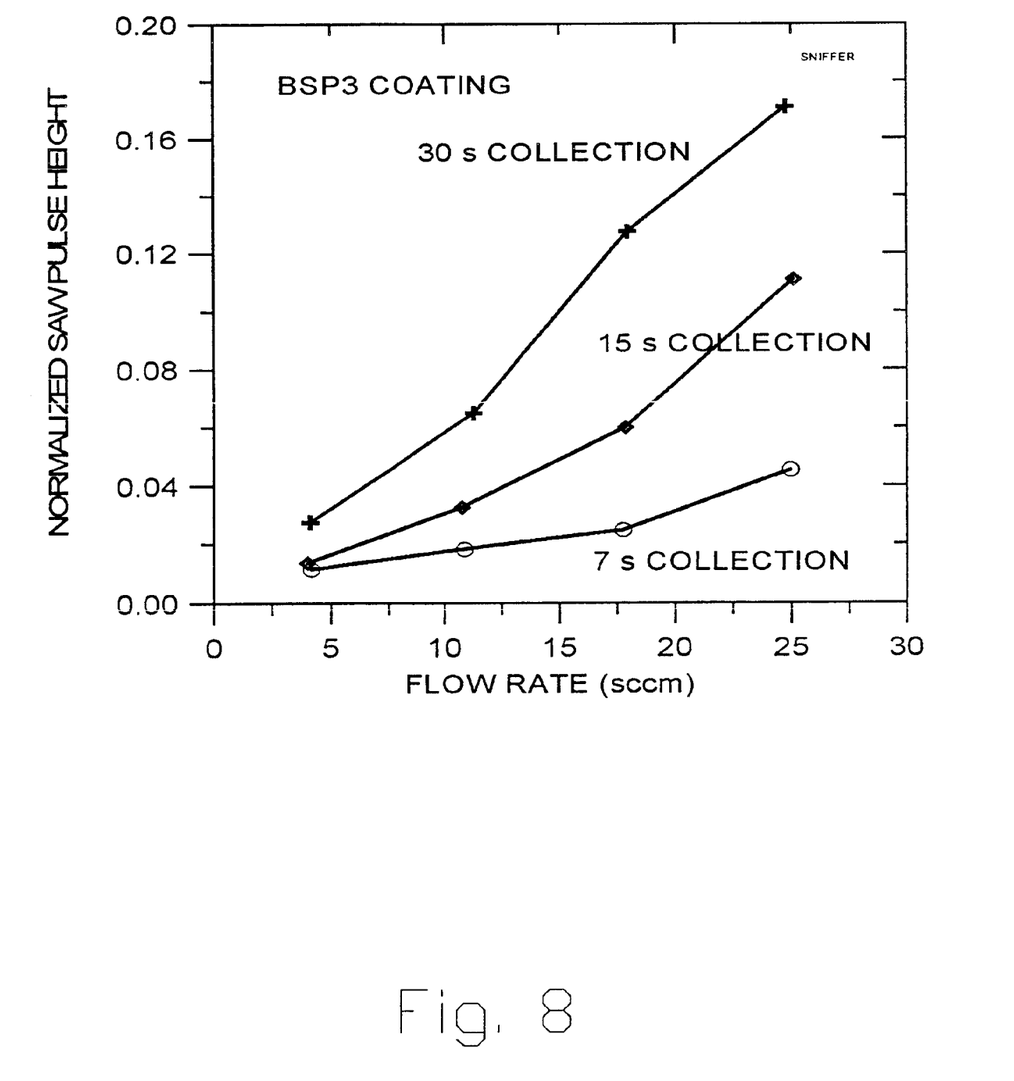

Because of this low drive pressure, it is necessary to make the flow channel as non-restrictive as possible. This need is counterbalanced by the need to minimize diffusion distances in the flow over the preconcentrator and SAW. In the ram-airflow channel shown in the drawings, the cross-sectional area is reduced over the preconcentrator and SAW detector, and then expanded again at the discharge (at the fourth section). The channel over the SAW is the most restrictive with dimensions in a preferred embodiment of 1.3-mm wide×0.1-mm high×2.3-mm long. Pressure drops through each section of the sensor can be estimated with the relationship $$\Delta P = \frac{12\mu \cdot length \cdot flowrate}{width(height)^3},$$

where $\mu$ is the air viscosity. By equating the pressure drop through the system to the available static pressure, an estimate can be made of the potential flow rate through the sensor. FIG. 7 shows the estimated volumetric flow rate through the sensor as a function of air speed. Measured results shown in FIG. 8 illustrate that flow rates through the sensor are sufficient to perform chemical analysis on the air stream. For these results, analytes in the air stream were allowed to collect on the preconcentrator for specified times of 7s, 15 s, and 30s. The preconcentrator was then thermally pulsed to desorb the analyte, and the concentrated analyte was transported across the SAW detector by the air flow. With a 15 second collection time and a 20 knot air speed, this combination of a SAW, a preconcentrator, and ram-air pumping is capable of detecting 1 ppm levels of analytes such as mustard gas and nerve agents.

Thus, it is seen that the objects of the present invention are efficiently obtained, although modifications and changes to the invention should be readily apparent to those having ordinary skill in the art, and these modifications are intended to be within the spirit and scope of the invention as claimed.

What I claim is:

1. In a surface acoustic wave sensor mounted within a body, said sensor having a surface acoustic wave array detector and a micro-fabricated sample preconcentrator exposed on a surface of said body, an apparatus for collecting air for said sensor, comprising:

a housing operatively arranged to mount atop said body, said housing including a passageway having an inlet and an outlet, said passageway having a first section of a first cross-sectional area proximate said inlet, a second section of a second cross-sectional area proximate said first section, a third section of a third cross-sectional area proximate said second section, and a fourth section of a fourth cross-sectional area proximate said outlet, where said third cross-sectional area is less than said second cross-sectional area, and said first and fourth cross-sectional areas are each larger than said second cross-sectional area.

2. The apparatus recited in claim 1 wherein said second section of said passageway communicates sampled air to said micro-fabricated sample preconcentrator.

3. The apparatus recited in claim 1 wherein said third section of said passageway communicates sampled air to said surface acoustic wave array detector.

4. The apparatus recited in claim 1 wherein said first cross-sectional area is substantially the same as said fourth cross-sectional area.

5. The apparatus recited in claim 1 wherein said first and fourth cross-sectional areas are the same.

6. The apparatus recited in claim 1 wherein said inlet is operatively arranged to be directed toward an oncoming stream of air to be sampled, and said outlet is operatively arranged to discharge sampled air into a low pressure region in air flow around said body.

7. The apparatus recited in claim 1 wherein said apparatus creates a pressure difference between said inlet and said outlet.

8. In a surface acoustic wave sensor mounted within a body, said sensor having a surface acoustic wave array detector and a micro-fabricated sample preconcentrator exposed on a surface of said body, an apparatus for collecting air for said sensor, comprising:

a housing operatively arranged to mount atop said body, said housing including a multi-stage channel having an inlet and an outlet, said channel having a first stage having a first height and width proximate said inlet, a second stage having a second lower height and width proximate said micro-fabricated sample preconcentrator, a third stage having a still lower third height and width proximate said surface acoustic wave array detector, and a fourth stage having a fourth height and width proximate said outlet, where said fourth height and width are substantially the same as said first height and width.

* * * * *

UNITED STATES PATENT AND TRADEMARK OFFICE
CERTIFICATE OF CORRECTION

PATENT NO. : 6,442,997 B1
DATED : September 3, 2002
INVENTOR(S) : Clifford A. Megerle, Douglas R. Adkins and Gregory C. Frye-Mason It is certified that error appears in the above-identified patent and that said Letters Patent is hereby corrected as shown below:

<u>Title page,</u>
Item [73], Assignee, add the following:

-- Lockheed Martin Corporation, Bethesda, Maryland (US)
Sandia Corporation, Albuquerque, New Mexico (US) --.

Signed and Sealed this

Twenty-third Day of September, 2003

JAMES E. ROGAN
*Director of the United States Patent and Trademark Office*